US008585982B1

(12) United States Patent
Quintana et al.

(10) Patent No.: US 8,585,982 B1
(45) Date of Patent: Nov. 19, 2013

(54) FIELD COLORIMETRIC TEST DEVICE

(75) Inventors: Roxanne L. Quintana, Ridgecrest, CA (US); Martin W. Krauss, Fort Myers, FL (US); Alvin L. Quintana, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/494,869

(22) Filed: Jun. 12, 2012

Related U.S. Application Data

(60) Provisional application No. 61/592,795, filed on Jan. 31, 2012.

(51) Int. Cl.
*G01N 21/01* (2006.01)
(52) U.S. Cl.
USPC ........... 422/413; 422/402; 422/430; 422/294; 422/295; 435/287.6; 435/288.2; 436/104; 436/165

(58) Field of Classification Search
USPC .............. 422/405–406, 413, 402, 430, 82.05; 435/287.6, 288.2; 436/104, 165
See application file for complete search history.

(56) References Cited

U.S. PATENT DOCUMENTS

| | | | | | |
|---|---|---|---|---|---|
| 4,562,043 | A | * | 12/1985 | Mennen et al. | 422/411 |
| 4,770,853 | A | * | 9/1988 | Bernstein | 422/413 |
| 4,788,039 | A | | 11/1988 | Glattstein | |
| 2006/0216833 | A1 | | 9/2006 | Pagoria et al. | |
| 2010/0093069 | A1 | * | 4/2010 | Squirrell | 435/287.2 |

* cited by examiner

*Primary Examiner* — Lyle Alexander
(74) *Attorney, Agent, or Firm* — James M. Saunders

(57) ABSTRACT

A field colorimetric test device includes a housing having at least one interior compartment. A sampling device is configured to be associated with a distal end of the housing. A selection device is attached to a proximal end of the housing.

11 Claims, 2 Drawing Sheets

US 8,585,982 B1

FIELD COLORIMETRIC TEST DEVICE

CROSS-REFERENCE TO RELATED APPLICATIONS

This is a non-provisional application claiming the benefit of parent provisional application No. 61/592,795 filed on Jan. 31, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to colorimetric test devices and, more particularly, to field grade test devices that do not require sophisticated testing techniques or extensive training.

Figures 1A, 1B:
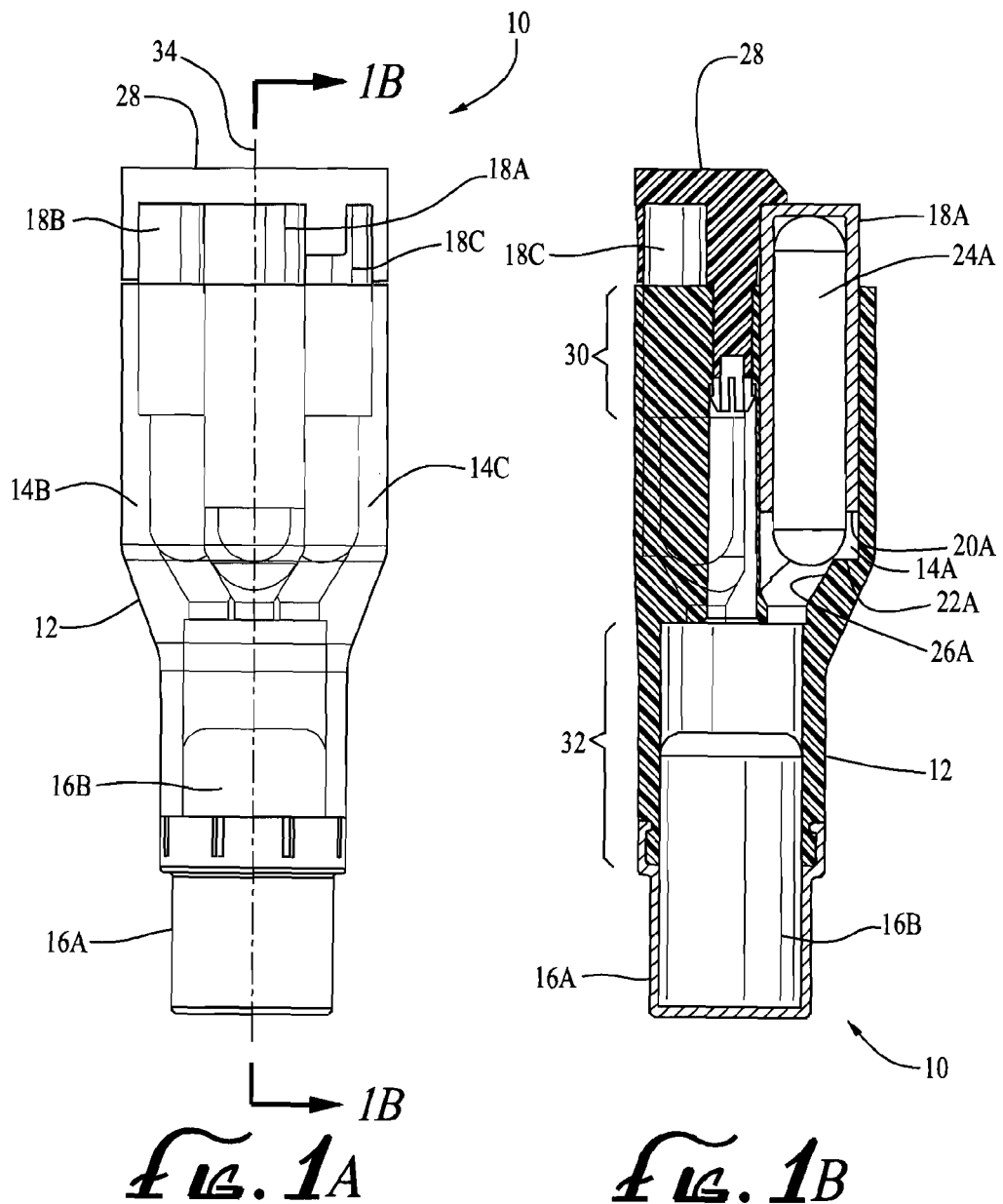
FIG. 1A is a side view of a field colorimetric test device, according to embodiments of the invention.
FIG. 1B is a partial section view of a field colorimetric test device, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to colorimetric test devices and, more particularly, to field grade test devices that do not require sophisticated testing techniques or extensive training.

War fighters need a way to test surfaces and unknown substances in the field to presumptively identify explosives, drugs, gunshot residue, and other substances that may indicate a potentially high risk situation. Testing devices are more user-friendly when they are small, simple, and easy to use.

Embodiments of the invention hold up to three test reagents. However, the potential for greater than three test reagents is possible depending on application-specific conditions. Additionally, embodiments of the invention do not require a sampling glove. This feature makes testing easier and less prone to sampler error. Embodiments of the invention can be used for presumptive colorimetric testing for virtually any substance with obvious colorimetric responses to liquid or solid reagents.

Embodiments of the invention are small and robust enough to fit several of the devices in a pocket or stacked in a small container. A sampling swab is in a cap, allowing the cap to act as a handle. The swab, therefore, is able to be used to collect a sample without being touched by a user's hand. The testing device body is transparent which allows sampling results to be observed without exposure of personnel to the reagents or the sample. Solid or liquid reagents can be included in breakable vials such as, for example, crushable glass or plastic ampoules. Including the reagents in individual ampoules increases shelf-life of the product. Additional solid reagents can be added, depending on application-specific conditions, to the swab or in one or more of the ampoule cavities.

Embodiments of the invention reduce the likelihood of error because the construction ensures that the reagent can only be added in a correct order. The construction reduces testing errors, even when the user's attention is divided.

After the sample is obtained, the testing device is closed and the sample is protected so that analysis can be done immediately or at a later time. Additionally, reagents are included during analysis, minimizing or eliminating exposure of personnel to hazards the reagents may present.

Although embodiments of the invention are described in considerable detail, including references to certain versions thereof, other versions are possible. Examples of other versions include positioning components in different orientations. Therefore, the spirit and scope of the appended claims should not be limited to the description of versions included herein.

Figure 2:
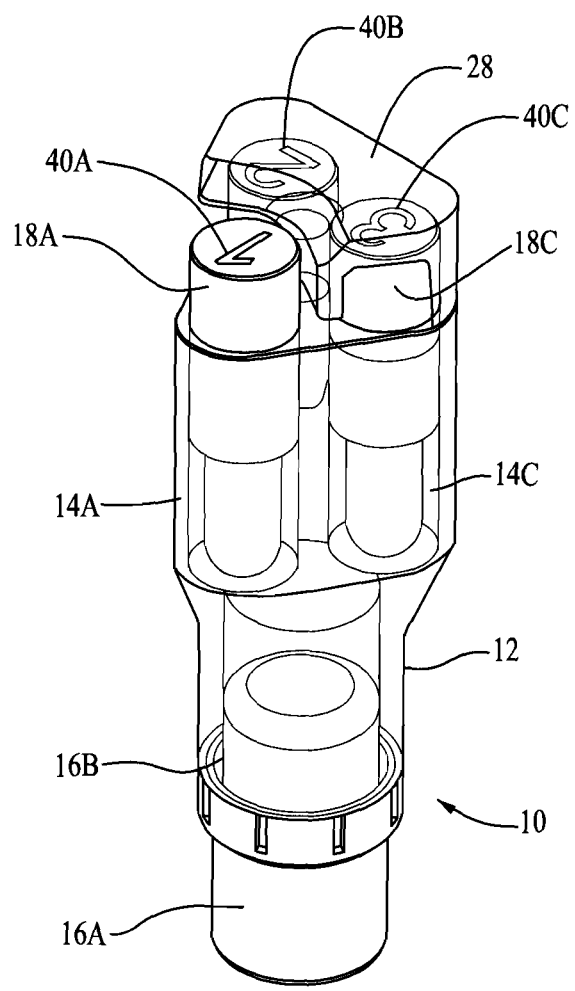
FIG. 2 is an elevation view of a field colorimetric test device, according to embodiments of the invention.

In the accompanying drawings, like reference numbers indicate like elements. FIG. 1A illustrates a side view of a field colorimetric test device, according to embodiments of the invention. FIG. 1B illustrates a partial section view of a field colorimetric test device, according to embodiments of the invention. FIG. 2 illustrates an elevation view of a field colorimetric test device, according to embodiments of the invention. Reference character 10 depicts an apparatus of embodiments of the invention.

Referring simultaneously to FIGS. 1A, 1B, and 2, embodiments of the invention generally relate to a protective system for a test device, including: a housing 12 having at least one interior compartment 14 (shown as 14A, B, and C). A sampling device (shown collectively as 16A and 16B) is configured to be associated with a distal end 32 of the housing 12.

At least one hollow vial 18 (shown as 18A, B, and C) is configured to fit in the housing 12. Specifically, each of the hollow vials 18 is configured to fit in a respective interior compartment associated with the interior compartments 14. Each of the hollow vials 18 has a first 20 and a second 22 position (shown as 20A and 22A, respectively, for ease of viewing in FIG. 1B).

At least one breakable ampoule 24 is configured to fit in the housing 12. Specifically, each of the breakable ampoules 24 (shown as 24A in FIG. 1B for ease of viewing) is configured to fit in a respective hollow vial 18. Each of the breakable ampoules 24 is configured to hold at least one chemical reagent (not shown).

At least one breaking device 26 is configured to fit in the housing 12. Specifically, each breaking device 26 (shown as 26A in FIG. 1B for ease of viewing) is configured at a bottom portion of a respective hollow vial 18. Each breaking device 26 is configured to break each of the respective breakable ampoules 24 when each of the hollow vials 18 is actuated to the second position 22 (22A in FIG. 1B). A selection device 28 is attached to a proximal end 30 of the housing 12.

The association of the sampling device 16A and 16B to the distal end 32 of the housing 12 is selected from several appropriate connection mechanisms dependent on application-specific conditions. The group of appropriate connection mechanisms includes removable connections, hinged connections, hitched connections, and capped connections. FIGS. 1A, 1B, and 2 depict a removable connection mechanism showing the sampling device 16A and 16B to be removably connected to the distal end 32 of the housing 12. The removable connection is friction-fit.

Another embodiment of the invention generally relates to a test device, including: a housing 12 having a first end 30 and second 32 end. The housing 12 is configured with at least one hollow interior compartment 14. A cap 16A is configured to be removably connected to the second end 32 of the housing 12. A sampling swab 16B is configured to be associated with the cap 16A. As shown in FIGS. 1A, 1B, and 2, the sampling swab 16B is connected inside the cap 16A.

At least one hollow vial 18 equal in number to the hollow interior compartments 14 are configured to fit in the hollow interior compartments. Specifically, each of the hollow vials 18 is configured to fit in a respective hollow interior compartment 14. Each of the hollow vials 18 has a first 20 and a second position 22. Each of the hollow vials 18 is configured to hold a chemical reagent (not shown).

At least one breaking device 26 is equal in number to the hollow vials 18 and is configured to fit at a bottom portion of a respective hollow vial and to break each of the hollow vials 18 when each of the hollow vials is actuated to the second position 22. A selection device 28 is attached to the first end 30 of the housing 12.

In yet another embodiment, the invention generally relates to a test device, including: a housing 12 having a first end 30, a second end 32, a first hollow interior compartment 14A, a second hollow interior compartment 14B, and a third hollow interior compartment 14C. A hollow cap 16A is configured to be associated with the second end 32 of the housing 12. A sampling swab 16B is configured to be associated with the hollow cap 16A. As shown in FIGS. 1A, 1B, and 2, the sampling swab 16B is connected inside the hollow cap 16A.

The association of the hollow cap 16A to the second end 32 of the housing 12 is selected from several appropriate connection mechanisms dependent on application-specific conditions. The group of appropriate connection mechanisms includes removable connections, hinged connections, hitched connections, and capped connections. FIGS. 1A, 1B, and 2 depict a removable connection mechanism showing the cap 16A to be removably connected to the second end 32 of the housing 12. The removable connection is friction-fit.

A first hollow vial 18A is configured to fit in the first hollow interior compartment 14A. The first hollow vial 18A has a first and a second position (depicted as 20A and 22A, respectively in FIG. 1B). A second hollow vial 18B is configured to fit in the second hollow interior 14B compartment. The second hollow vial 18B has a first 20 and a second 22 position (positions not shown for ease of viewing). A third hollow vial 18C is configured to fit in the third hollow interior compartment 14C. The third hollow vial 18C has a first and a second position (positions not shown for ease of viewing).

A first crushable ampoule 24A is configured to fit inside the first hollow vial 14A. The first crushable ampoule 24A is configured to hold a first chemical reagent (not shown). A second crushable ampoule (not shown) is configured to fit inside the second hollow vial 18B. The second crushable ampoule (not shown) is configured to hold a second chemical reagent (not shown). A third crushable ampoule (not shown) is configured to fit inside the third hollow vial 18C. The third crushable ampoule (not shown) is configured to hold a third chemical reagent (not shown).

A first breaking device 26A is configured at a bottom portion of the first hollow vial 14A. The first breaking device 26A is configured to break the first crushable ampoule 24A when the first hollow vial 18A is actuated to the second position 22A.

A second breaking device (not shown) is configured at a bottom portion of the second hollow vial 18B. The second breaking device (not shown) is configured to break the second crushable ampoule (not shown) when the second hollow vial 18B is actuated to the second position (not shown).

A third breaking device (not shown) is configured at a bottom portion of the third hollow vial 18C. The third breaking device (not shown) is configured to break the third crushable ampoule (not shown) when the third hollow vial 18C is actuated to the second position (not shown). A selection device 28 is attached to the first end 30 of the housing 12.

A first actuator is an upper portion 40A (FIG. 2) of the first hollow vial 18A. A second actuator is an upper portion 40B (FIG. 2) of the second hollow vial 18B. A third actuator is an upper portion 40C (FIG. 2) of the third hollow vial 18C.

In embodiments, the sampling device (shown as 16A and 16B) includes a cap 16A and a sampling swab 16B. The cap 16A is hollow. The sampling swab 16B is configured to be connected inside the hollow cap 16A. The sampling swab 16B is configured to adhere test samples and change color when exposed to the chemical reagent when the test samples are target substances.

In embodiments, the housing 12 is transparent and is appropriately sized to provide at least one area for including instructions. The area for instructions is any portion of the side of the housing 12. However, an area for instructions may, as an alternative to an area for including instructions on the housing 12, be appropriately sized and positioned elsewhere on the apparatus 10 such as, for example, on the cap 16A. The instructions may be color labels assisting the user in determining whether a particular chemical is present after testing. Similarly, the apparatus 10 may be included in a kit or pouch and may include more detailed instructions within the kit or pouch.

In embodiments, the upper portion 40A, B, and C (FIG. 2) of each hollow vial of the plurality of hollow vials 18 is a respective actuator configured to move each hollow vial of the plurality of hollow vials from the first position 20 to the second position 22 when the upper portion of each hollow vial is subjected to force. Actuation is done by exerting force such as, for example, with the user's finger on the respective upper portion 40A, B, and C of the respective vial 18.

In embodiments, the selection device 28 is transparent and is a dial configured to rotate axially in one direction about a central longitudinal axis 34. The selection device 28 exposes one of the upper portions 40A, B, and C of the hollow vials 18 and covers the others. The transparency of the selection device 28 allows the user to see the upper portions 40A, B, and C that are covered. Prior to first use, the selection device 28 is positioned such that the upper portion 40A associated with the first hollow vial 18A is exposed and upper portions 40B and C are covered by the selection device.

In embodiments, the selection device 28 rotation is either clockwise or counterclockwise. As depicted in FIG. 2, rotation of the selection device 28 is clockwise, although as discussed above, counterclockwise rotation is possible with associated reorientation of the hollow vials 18A, B, and C. This feature assures that reagents are added in the proper sequence. Thus, in an embodiment, the user will depress the upper portion 40A associated with hollow vial 18A holding reagents associated with a first chemical test series. The user may then turn the selection device 28 and depress the upper portion 40B associated with hollow vial 18B holding reagents associated with a second chemical test series. The user may then turn the selection device 28 and depress the upper portion 40C associated with hollow vial 18C holding reagents associated with a third chemical test series.

In embodiments, the upper portion (40A, B, and C) may be labeled with numerals, letters, or other appropriate labeling designating the first, second, and third chemical test series (and possibly more depending on application-specific conditions) and for assisting with using the apparatus 10.

In embodiments, the breakable ampoules 24 may be referred to as crushable ampoules and are selected from the group of breakable materials consisting of crushable glass and crushable plastic. Other suitable materials may also be used based on application-specific conditions.

In embodiments, the breakable ampoule 24 is in fluid communication with the swab 16B when the ampoule is broken because the housing 12 is hollow, allowing a pathway for the chemical reagents to travel. The reagent will then mix with the swab 16B including the adhered to test samples. Likewise, in embodiments where the hollow vials 18 include the reagent, the hollow vials are in fluid communication with the swab 16B when the hollow vials are broken.

In embodiments, components are configured and appropriately-dimensioned to allow proper fit, orientation, and movement. Examples include the following: hollow vial 18A fits in interior compartment 14A (FIGS. 1A and 3), crushable ampoule 24A fits in hollow vial 18A (FIG. 1B), and breaking device 26A is an angular feature of the interior compartment 14A and is located at the bottom of crushable ampoule 24A (FIG. 1B).

In embodiments, sampling gloves are not needed. Likewise, a horizontal surface such as, for example, a table is not needed for staging.

In embodiments, additional reagents may be added to the hollow vials 18 depending on application-specific conditions without detracting from the merits or generality of embodiments of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A field colorimetric test device, comprising:
   a housing having a proximal end, a distal end, a central longitudinal axis, and at least one interior compartment;
   a sampling device configured to be associated with said distal end of said housing;
   at least one hollow vial, wherein each of said at least one hollow vial is configured to fit in a respective interior compartment associated with said at least one interior compartment, wherein each of said at least one hollow vial has a first and a second position;
   at least one breakable ampoule, wherein each of said at least one breakable ampoule is configured to fit in a respective hollow vial associated with said at least one hollow vial, wherein each of said at least one breakable ampoule is configured to hold at least one chemical reagent;
   at least one breaking device, wherein each of said at least one breaking device is configured at a bottom portion of a respective hollow vial associated with each of said at least one hollow vial, wherein each of said at least one breaking device is configured to break each of said at least one breakable ampoule when each of said at least one hollow vial is actuated to said second position;
   wherein each of said breaking devices are integrally formed in each of said at least one interior compartment; and
   a rotary selection dial axially-attached to said proximal end of said housing, about said central longitudinal axis, wherein said rotary selection dial is configured to rotate axially about said central longitudinal axis between each of said at least one interior compartment.

2. The test device according to claim 1, wherein said sampling device is a friction-fit connection to said distal end of said housing, said sampling device, further comprising:
   a hollow cap; and
   a sampling swab configured to be associated with said hollow cap, wherein said sampling swab is configured to adhere test samples and change color when exposed to said chemical reagent(s) when said test samples are target substances.

3. The test device according to claim 1, wherein a portion of said housing is transparent and is sized to provide at least one area for including instructions.

4. The test device according to claim 1, wherein an upper portion of each of said at least one hollow vial is a respective actuator configured to move each of said at least one hollow vial from said first position to said second position when said upper portion of each of said at least one hollow vial is subjected to force.

5. The test device according to claim 1, wherein said at least one breakable ampoule is selected from the group of breakable materials consisting of crushable glass and crushable plastic.

6. A field colorimetric test device, comprising:
   a housing having a first end, a second end, a central longitudinal axis, a first hollow interior compartment, a second hollow interior compartment, and a third hollow interior compartment;
   a hollow cap configured to be associated with said second end of said housing;
   a sampling swab configured to be associated with said hollow cap;
   a first hollow vial configured to fit in said first hollow interior compartment, wherein said first hollow vial has a first and a second position;
   a second hollow vial configured to fit in said second hollow interior compartment, wherein said second hollow vial has a first and a second position;
   a third hollow vial configured to fit in said third hollow interior compartment, wherein said third hollow vial has a first and a second position;
   a first crushable ampoule configured to fit inside said first hollow vial, wherein said first crushable ampoule is configured to hold a first chemical reagent;

a second crushable ampoule configured to fit inside said second hollow vial, wherein said second crushable ampoule is configured to hold a second chemical reagent;

a third crushable ampoule configured to fit inside said third hollow vial, wherein said third crushable ampoule is configured to hold a third chemical reagent;

a first breaking device configured at a bottom portion of said first hollow vial, wherein said first breaking device is configured to break said first crushable ampoule when said first hollow vial is actuated to said second position;

a second breaking device configured at a bottom portion of said second hollow vial, wherein said second breaking device is configured to break said second crushable ampoule when said second hollow vial is actuated to said second position;

a third breaking device configured at a bottom portion of said third hollow vial, wherein said third breaking device is configured to break said third crushable ampoule when said third hollow vial is actuated to said second position;

wherein each of said breaking devices are integrally formed in each of said interior compartments; and a rotary selection dial axially-attached to said first end of said housing, about said central longitudinal axis, wherein said rotary selection dial is configured to rotate axially about said central longitudinal axis between each of said interior compartments.

7. The test device according to claim 6, wherein said housing is transparent and is sized to provide at least one area for including instructions.

8. The test device according to claim 6, wherein said hollow cap is a friction-fit connection to said second end of said housing.

9. The test device according to claim 6, wherein each of said crushable ampoule is selected from the group of crushable materials consisting of crushable glass and crushable plastic.

10. The test device according to claim 6, further comprising:
 a first actuator configured at an upper portion of said first hollow vial;
 a second actuator configured at an upper portion of said second hollow vial; and
 a third actuator configured at an upper portion of said third hollow vial.

11. The test device according to claim 6, wherein said swab is configured to adhere test samples and change color when exposed to said chemical reagents when said test samples are target substances.

* * * * *